US010126190B2

(12) United States Patent
Soeda et al.

(10) Patent No.: US 10,126,190 B2
(45) Date of Patent: Nov. 13, 2018

(54) CAPACITIVE FORCE SENSOR AND GRASPING DEVICE

(71) Applicant: CANON KABUSHIKI KAISHA, Tokyo (JP)

(72) Inventors: Yasuhiro Soeda, Yokohama (JP); Yasuhiro Shimada, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/310,421

(22) PCT Filed: Apr. 24, 2015

(86) PCT No.: PCT/JP2015/002233
§ 371 (c)(1),
(2) Date: Nov. 10, 2016

(87) PCT Pub. No.: WO2015/174030
PCT Pub. Date: Nov. 19, 2015

(65) Prior Publication Data
US 2017/0074734 A1    Mar. 16, 2017

(30) Foreign Application Priority Data

May 14, 2014    (JP) ................................. 2014-100982

(51) Int. Cl.
*G01L 5/22*        (2006.01)
*G01L 1/14*        (2006.01)
(Continued)

(52) U.S. Cl.
CPC .............. *G01L 5/228* (2013.01); *G01L 1/144* (2013.01); *G01L 1/146* (2013.01); *G01L 1/148* (2013.01);
(Continued)

(58) Field of Classification Search
CPC ... B06B 1/0292; B06B 1/0215; G01L 9/0072; G01L 9/0073; G01L 9/0086;
(Continued)

(56) References Cited

U.S. PATENT DOCUMENTS 6,945,115 B1 *   9/2005   Wang .................... G01L 9/0073
                                                    73/718
7,493,821 B2 *   2/2009   Wang .................... H04R 19/00
                                                    361/283.2
(Continued)

FOREIGN PATENT DOCUMENTS

EP      2578141 A1    4/2013
JP      S63128236 A   5/1988
(Continued)

*Primary Examiner* — Jonathan Dunlap
(74) *Attorney, Agent, or Firm* — Canon U.S.A.Inc., IP Division

(57) ABSTRACT

A capacitive force sensor 101 of the present invention includes a plurality of cells each including a lower electrode 104, a movable member that includes an upper electrode 107 and has flexibility, and a support 105b arranged to movably support the movable member and to form a gap 106 between the upper and the lower electrodes. The plural cells are grouped into elements each including one or more of the cells, and the one or more cells in a same element are electrically connected to each other.

13 Claims, 4 Drawing Sheets

(51) Int. Cl.
  *G01L 9/00* (2006.01)
  *B06B 1/02* (2006.01)
  *G01N 29/24* (2006.01)

(52) U.S. Cl.
  CPC ........... *B06B 1/0215* (2013.01); *B06B 1/0292* (2013.01); *G01L 9/0072* (2013.01); *G01L 9/0073* (2013.01); *G01L 9/0086* (2013.01); *G01N 29/2406* (2013.01); *G05B 2219/39107* (2013.01); *G05B 2219/39508* (2013.01); *G05B 2219/39527* (2013.01)

(58) Field of Classification Search
  CPC ........... G05B 2219/39107; G05B 2219/39508; G05B 2219/39527; G01N 29/2406
  USPC .......... 73/718, 724, 715; 310/300, 309, 311, 310/317, 323.19, 336
  See application file for complete search history.

(56) References Cited

U.S. PATENT DOCUMENTS

| | | | | |
|---|---|---|---|---|
| 8,250,926 B2* | 8/2012 | Yang | ........................ | G01L 1/142 73/715 |
| 8,256,302 B2* | 9/2012 | Fujii | ........................ | G01H 11/06 73/718 |
| 8,378,436 B2* | 2/2013 | Ezaki | ........................ | B06B 1/0292 257/416 |
| 8,466,522 B2* | 6/2013 | Ezaki | ........................ | B06B 1/0292 257/416 |
| 8,515,579 B2* | 8/2013 | Alcazar | ........................ | B25J 9/1669 700/258 |
| 8,531,919 B2* | 9/2013 | Cheng | ........................ | B06B 1/0292 367/181 |
| 8,654,614 B2* | 2/2014 | Kandori | ........................ | B06B 1/0292 310/309 |
| 8,760,031 B2* | 6/2014 | Chang | ........................ | B06B 1/0292 257/416 |
| 8,869,622 B2* | 10/2014 | Fujii | ........................ | B06B 1/0292 73/718 |
| 9,120,126 B2* | 9/2015 | Hong | ........................ | H01L 23/481 |
| 9,546,923 B2* | 1/2017 | Kautzsch | ........................ | G01L 9/0073 |
| 2005/0075572 A1* | 4/2005 | Mills | ........................ | B06B 1/0292 600/459 |
| 2006/0230835 A1* | 10/2006 | Wang | ........................ | H04R 19/00 73/718 |
| 2008/0173094 A1* | 7/2008 | Shikata | ........................ | A61B 8/4494 73/625 |
| 2009/0001853 A1* | 1/2009 | Adachi | ........................ | A61B 8/4483 310/323.19 |
| 2009/0031825 A1 | 2/2009 | Kishida | | |
| 2010/0201222 A1* | 8/2010 | Adachi | ........................ | A61B 8/4483 310/317 |
| 2010/0256498 A1* | 10/2010 | Tanaka | ........................ | B06B 1/0215 600/459 |
| 2010/0283354 A1* | 11/2010 | Soeda | ........................ | B81C 1/00476 310/300 |
| 2011/0005325 A1* | 1/2011 | Yang | ........................ | G01L 1/142 73/724 |
| 2011/0068654 A1* | 3/2011 | Cheng | ........................ | B06B 1/0292 310/300 |
| 2011/0073968 A1 | 3/2011 | Ezaki | | |
| 2011/0084570 A1* | 4/2011 | Soeda | ........................ | B06B 1/0292 310/300 |
| 2011/0137463 A1* | 6/2011 | Alcazar | ........................ | B25J 9/1669 700/259 |
| 2012/0010538 A1* | 1/2012 | Dirksen | ........................ | A61B 8/00 601/2 |
| 2012/0103096 A1* | 5/2012 | Kandori | ........................ | H04R 19/00 73/632 |
| 2012/0163124 A1* | 6/2012 | Akiyama | ........................ | B06B 1/0292 367/87 |
| 2012/0256519 A1* | 10/2012 | Tomiyoshi | ........................ | B06B 1/0292 310/300 |
| 2012/0262770 A1* | 10/2012 | Torashima | ........................ | G01N 29/2418 359/199.2 |
| 2012/0266682 A1* | 10/2012 | Torashima | ........................ | B06B 1/0292 73/715 |
| 2013/0256817 A1* | 10/2013 | Ezaki | ........................ | B06B 1/0292 257/416 |
| 2013/0302934 A1* | 11/2013 | Kato | ........................ | B06B 1/0292 438/53 |
| 2013/0313663 A1* | 11/2013 | Kato | ........................ | H01L 29/84 257/416 |

FOREIGN PATENT DOCUMENTS

| | | |
|---|---|---|
| JP | H02-068967 A | 3/1990 |
| JP | H0465645 A | 3/1992 |
| JP | H06-307960 A | 11/1994 |
| JP | 2000-022172 A | 1/2000 |
| JP | 2001-235382 A | 8/2001 |
| JP | 2003-043078 A | 2/2003 |
| JP | 2005-249644 A | 9/2005 |
| JP | 2006-250705 A | 9/2006 |
| JP | 2010-153821 A | 7/2010 |
| JP | 2010-272956 A | 12/2010 |
| JP | 2013068503 A | 4/2013 |
| JP | 2013-096870 A | 5/2013 |
| WO | 2011/021358 A2 | 2/2011 |
| WO | 2012/108283 A2 | 8/2012 |
| WO | 2013/145478 A1 | 10/2013 |

* cited by examiner

[Fig. 1A]
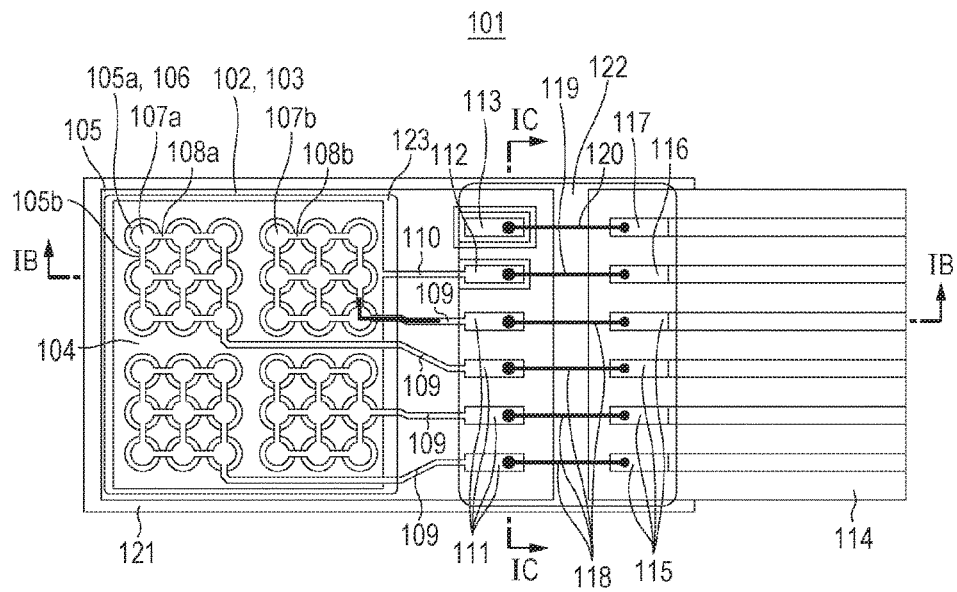
[Fig. 1B]
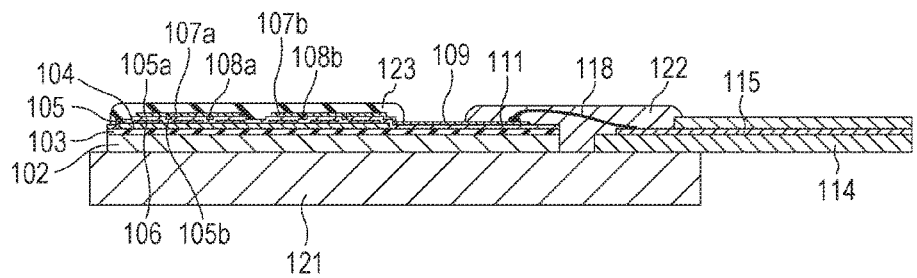
[Fig. 1C]
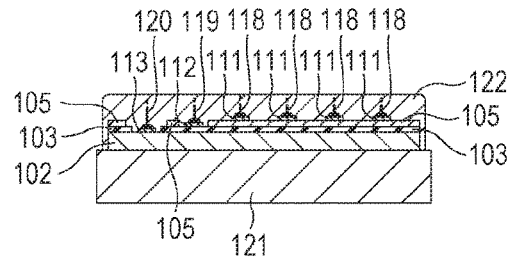

[Fig. 2A]
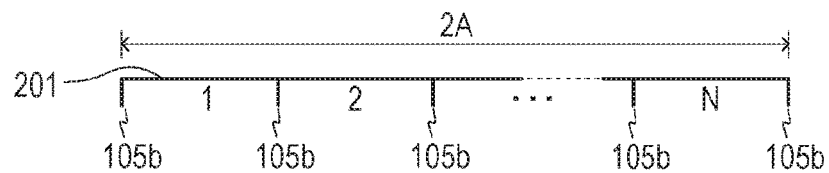
[Fig. 2B]
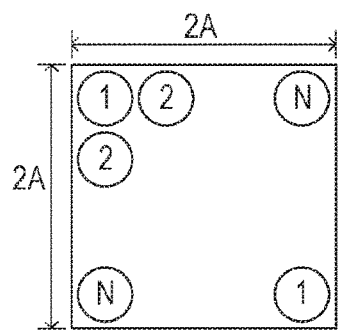
[Fig. 2C]
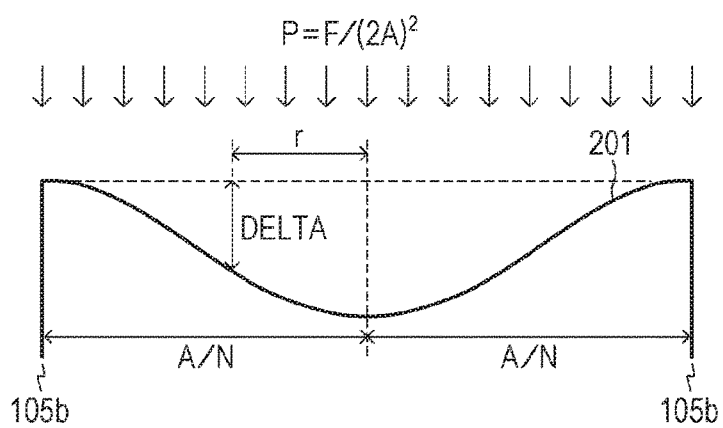

[Fig. 3A]
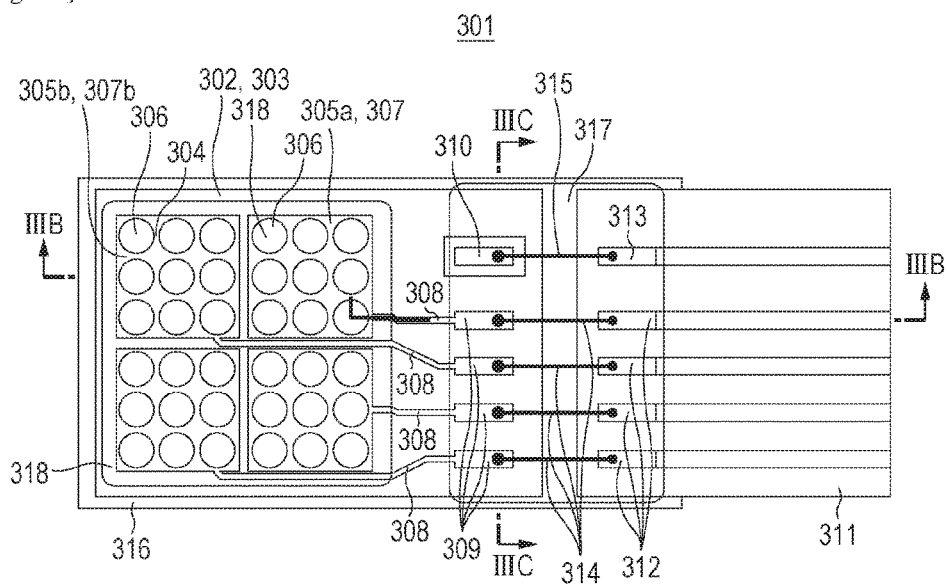
[Fig. 3B]
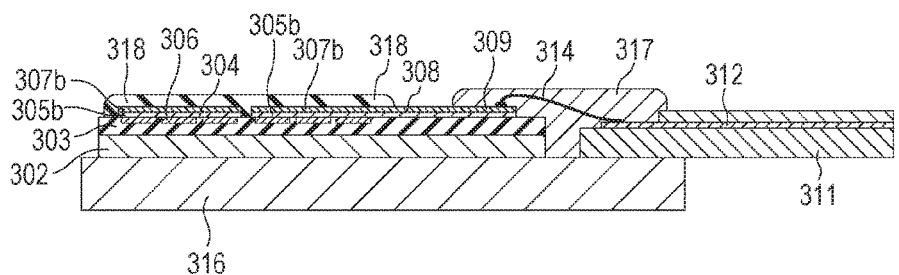
[Fig. 3C]
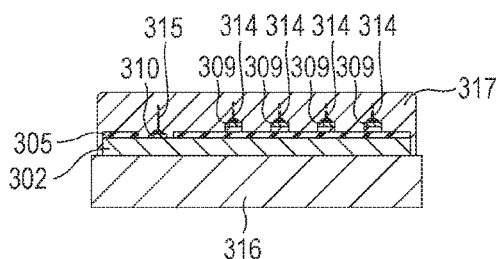

[Fig. 4]
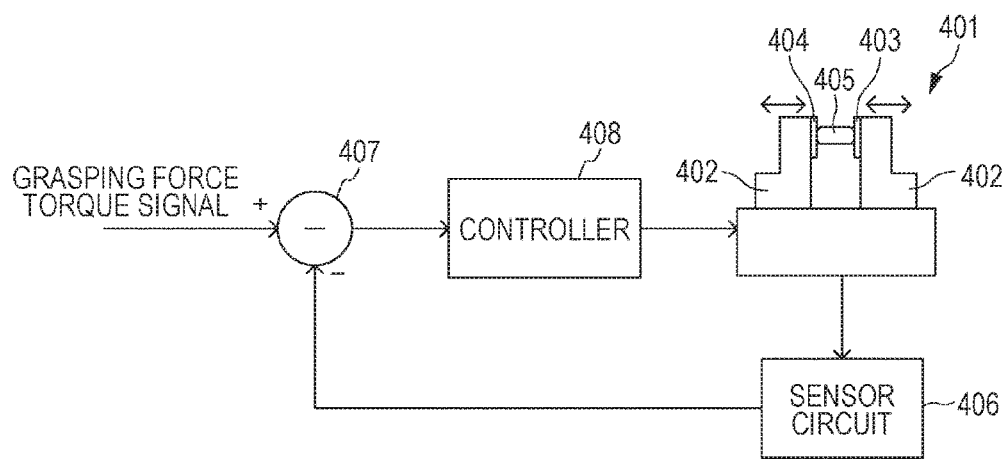

CAPACITIVE FORCE SENSOR AND GRASPING DEVICE

CROSS-REFERENCE TO RELATED APPLICATIONS

This application is a National Stage filing of International Application No. PCT/JP2015/002233 filed Apr. 24, 2015, which claims the benefit of Japanese Patent Application No. 2014-100982, filed May 14, 2014, the disclosures of each of which are hereby incorporated by reference herein in their entirety.

TECHNICAL FIELD

The present invention relates to a force sensor that detects, e.g., a contact load with respect to a material object, such as a solid body having certain rigidity. The present invention further relates to a grasping device using the force sensor.

BACKGROUND ART

A force sensor is applied, for example, to detect a grasping force of a robot hand that is used in lines for manufacturing products. Here, the grasping implies an operation of firmly holding a workpiece by a robot hand. An increase of accuracy in control of the grasping force is expected by detecting the grasping force of the robot hand, and by performing feedback control on the grasping force, which is applied to the workpiece, in accordance with detected information.

A capacitive force sensor is known as one of various types of force sensors for detecting contact loads. In a typical structure of the capacitive force sensor, a membrane having flexibility is movably disposed on a substrate with a support member (also called a spacer or a post in this specification) interposed between them. An electrode is disposed in each of the membrane and the substrate (in this specification, the electrode on the membrane side is called an upper electrode and the electrode on the substrate side is called a lower electrode), and the upper electrode is deformable together with the membrane. When a load is applied to the membrane upon contact with a solid body, for example, the membrane is caused to flex, and the distance between the upper and lower electrode is changed. The magnitude of the applied load is detected by detecting the distance between the upper and lower electrode in terms of capacitance, and by converting the detected capacitance to an electric signal. A structure unit constituted by the membrane, the upper and lower electrodes, and the spacer is called a cell.

Force sensors are grouped, from the viewpoint of function, into a type of measuring a load, a type of measuring load distribution, and a type of measuring the direction of a load (e.g., tensile direction, compression direction, or shearing direction). In any type, the shape or the structure of a sensor surface is constituted such that a deformable portion of a detection device is deformed selectively with respect to a load applied in a direction or a position to be detected. In a related-art force sensor, a unit device for detection (i.e., a detection unit device) is constituted by one cell (see PTL 1).

In a force sensor used to detect a grasping force of an assembly robot, a contact surface with respect to a workpiece functions as not only a sensor, but also as a mechanical member for grasping the workpiece. When the sensor surface is deformed due to a load applied to the force sensor, such deformation may be one of factors causing a shift of the position at which the workpiece is grasped. Accordingly, there is a demand for a force sensor in which the deformable portion in the sensor surface is deformed in a small amount due to the load.

CITATION LIST

Patent Literature

PTL 1: Japanese Patent Laid-Open No. 2006-250705

SUMMARY OF INVENTION

Technical Problem

In the related-art force sensor, however, because the detection unit device is constituted by one cell, an area of the membrane in the cell depends on an area of the detection device. Accordingly, when the area of the detection device increases, the area of the membrane also increases. This may result in that the amount of deformation of the membrane per unit load is increased.

Solution to Problem

In view of the above-mentioned problems, the present invention is constituted as follows. A capacitive force sensor includes a plurality of cells each including a lower electrode (second electrode), a movable member that includes an upper electrode (first electrode) and has flexibility, and a support arranged to movably support the movable member and to form a gap between the upper electrode and the lower electrode, wherein the plural cells are grouped into elements each including at least one of the cells, and the one or more cells in a same element are electrically connected to each other. As an alternative, a capacitive force sensor includes a plurality of elements each including a lower electrode, a movable member that includes an upper electrode and has flexibility, and a support arranged to movably support the movable member and to form a gap between the upper electrode and the lower electrode, wherein the support is made up of plural parts, the movable member, the upper electrode, and the gap are each separated into plural parts corresponding to the plural parts of the support, and the plural parts of the upper electrode in each of the elements are electrically connected to each other.

Further features of the present invention will become apparent from the following description of exemplary embodiments with reference to the attached drawings.

BRIEF DESCRIPTION OF DRAWINGS

FIG. 1A is an illustration to explain a first embodiment of the present invention.

FIG. 1B is an illustration to explain the first embodiment of the present invention.

FIG. 1C is an illustration to explain the first embodiment of the present invention.

FIG. 2A is an illustration to explain operation and advantageous effects of the present invention.

FIG. 2B is an illustration to explain operation and advantageous effects of the present invention.

FIG. 2C is an illustration to explain operation and advantageous effects of the present invention.

FIG. 3A is an illustration to explain a second embodiment of the present invention.

FIG. 3B is an illustration to explain the second embodiment of the present invention.

FIG. 3C is an illustration to explain the second embodiment of the present invention.

FIG. 4 is an illustration to explain a third embodiment of the present invention.

DESCRIPTION OF EMBODIMENTS

In the present invention, a detection unit device of a force sensor is constituted by a plurality of cells (or plural regions in an element), which are electrically connected in parallel. At least a part of the element may be covered with a surface material made of an elastic body having a smaller longitudinal elasticity modulus than a support. Here, the plural cells are grouped into a plurality of elements each including at least one of the cells, and the one or more cells in the same element are electrically connected to each other. Alternatively, in the same element, plural parts of an upper electrode (first electrode) are electrically connected to each other. The expression "the cells are electrically connected to each other" typically implies that upper electrodes (first electrodes) and lower electrodes (second electrodes) corresponding to the cells are electrically connected to each other for each of upper and lower sides. When there are plural elements, at least ones of the upper electrodes and the lower electrodes are electrically separated from each other between the different elements. Thus, an area of a membrane constituting a movable member can be designed freely or flexibly with respect to an area of the detection unit device. A deformation amount of the membrane with respect to a unit load can be reduced by designing the area of the membrane to a smaller value. As a result, a force sensor can be realized in which an amount of surface deformation with respect to the load is relatively small. When the force sensor is disposed on, e.g., a grasping portion of an assembly robot to detect a load attributable to a grasping force, for example, surface deformation of the force sensor tends to cause reduction of accuracy in, e.g., a position at which an object to be handled, such as a workpiece, is grasped. However, the reduction of the accuracy is avoided by the force sensor of the present invention in which the amount of surface deformation with respect to the load is relatively small.

Embodiments of the present invention will be described below with reference to the drawings.

First Embodiment

FIGS. 1A, 1B and 1C are illustrations to explain a first embodiment of a capacitive force sensor according to the present invention. FIG. 1A is a plan view, FIG. 1B is a sectional view taken along IB-IB, and FIG. 1C is a sectional view taken along IC-IC.

A force sensor 101 includes a substrate 102, an insulating layer 103, a lower electrode 104, a membrane layer 105, a gap 106, an upper electrode 107, an upper electrode wiring 108, lead wirings 109 and 110, and pads 111, 112 and 113. The force sensor 101 further includes a flexible substrate 114, pads 115, 116 and 117, wires 118, 119 and 120, a device board 121, a wire protection member 122, and an elastic body 123. The upper electrode 107, the upper electrode wiring 108, the lead wiring 109, the pad 111, the pad 115, and the wire 118 are each disposed in plural number in the force sensor 101. When individual parts of each of those components are to be discriminated for the sake of explanation, they are denoted as 107a and 107, for example, in the case of the upper electrode 107.

The substrate 102 is a plate-like material made of single-crystal silicon, and the insulating layer 103 is formed on the substrate 102. The insulating layer 103 can be formed by thermally oxidizing the substrate 102 made of single-crystal silicon. The lower electrode 104 is formed on the insulating layer 103. The lower electrode 104 can be formed by vacuum deposition of Al. The membrane layer 105 is a silicon nitride film or a silicon oxide film, which is formed by the plasma CVD method. A part of the membrane layer 105 is supported to the lower electrode 104 with a gap 106 interposed between them. Such a structure of the membrane layer 105 can be obtained by first forming a Cr layer (sacrificial layer) that has the same shape as that of the gap 106, forming the membrane layer 105 on the Cr layer, and thereafter removing the Cr layer by etching. A part of the membrane layer 105, the part being positioned above the gap 106, is called a membrane 105a, and a part of the membrane layer 105, the part serving as a sidewall of the gap 106, is called a sidewall portion (support) 105b. The silicon nitride film and the silicon oxide film are easy to form, and they can be each easily obtained at required levels of flexibility and rigidity. The upper electrode 107 is an electrode formed on the membrane layer 105, and it can be formed by vacuum deposition of Al.

In the structure of FIG. 1A, the gap 106 has a circular shape, for example. A typical diameter of the gap 106 is from 10 micrometers to several hundred micrometers, and a typical thickness of the membrane 105a is from 100 nanometers to several micrometers. A typical thickness of the upper electrode 107 is from 10 nanometers to several micrometers. Accordingly, the membrane 105a has flexibility together with the upper electrode 107. Note that the above-mentioned ranges of the diameter and the thickness are to be taken as illustrative and not as restrictive. The lower electrode 104, the membrane 105a, and the upper electrode 107, which are disposed around one gap 106, constitute a cell that is a minimum constituent unit of a detection device for detecting a load. One force sensor 101 includes a plurality of cells.

In the example of FIG. 1, the lower electrodes 104 for all the cells are electrically connected to each other. On the other hand, the upper electrodes 107 are electrically connected to each other by the upper electrode wiring 108 within each of separate groups of the upper electrodes 107. In the example of FIG. 1, nine upper electrodes 107a are electrically connected by an upper electrode wiring 108a. Similarly, nine upper electrodes 107b are electrically connected by an upper electrode wiring 108b. While FIG. 1 illustrates the example in which nine cells are electrically connected to each other, the number of connectable cells is not limited to a particular number. Because the upper electrode wiring 108 can be formed by vacuum deposition of Al, the upper electrode wiring 108 can be formed in the same step as the step of forming the upper electrodes 107. An assembly (group) of cells in which not only the lower electrodes, but also the upper electrodes are electrically connected to each other is called an element. In other words, the element is constituted by connecting a plurality of variable capacitors in parallel, and is a minimum unit for detection of the load. The force sensor 101 is required to include one or more elements, but a load distribution can be measured by arranging the element in plural number. FIG. 1A illustrates the example in which two elements are arranged in the direction of each side of the force sensor. However, a configuration where one element is constituted by one cell is also involved in the present invention.

The upper electrodes 107 in each element are led out to the pad 111 through the upper-electrode lead wiring 109. The lower electrode 104 is led out to the pad 112 through the lower-electrode lead wiring 110. The membrane layer 105 is opened at a position above the pad 113 such that the surface of the pad 112 is exposed to the outside. Furthermore, the pad 113 is formed on the substrate 102. The insulating layer 103 and the membrane layer 105 are opened in a region corresponding to the pad 113 such that the surface of the pad 113 is exposed to the outside. The pad 113 is used for grounding the substrate 102. The pads 111, 112 and 113 can be formed by vacuum deposition of Al together with the upper electrode wiring 108 after forming the required openings in the insulating layer 103 and the membrane layer 105. Thus, the pads 111, 112 and 113 can be formed in the same step as the step of forming the upper electrodes 107.

The substrate 102 is fixed onto the device board 121. The flexible substrate 114 is also fixed onto the device board 121. On the flexible substrate 114, the pads 115, 116 and 117 are disposed in opposing relation to the pads 111, 112 and 113, respectively, and the former pads are connected to the latter pads through the wires 118, 119 and 120, respectively. The wire protection member 122 is disposed around those wires to reduce damage that may be caused by external environments.

A surface material made of the elastic body 123 is coated over an upper surface in a region where the cells are arranged. The elastic body 123 has the function of distributing, to the membrane layer 105, a load that is applied upon the workpiece contacting with the sensor surface. With the function of the elastic body 123, even when the surface of the workpiece contacts with a membrane sidewall 105b and impedes deformation of the membrane 105a, the load can be detected because the elastic body 123 is deformed along the membrane 105a and the membrane 105a is hence deformed. Thus, the surface material made of the elastic body 123 is preferably a material having a smaller longitudinal elasticity modulus smaller than a film of silicon nitride or silicon oxide that is the material of the sidewall 105b. In practice, the surface material is selected from among silicone rubber, EPDM (ethylene-propylene rubber), PDMS (poly(dimethylsiloxane)), and urethane rubber.

The force sensor of this embodiment is featured in that plural cells are electrically connected to function as one element (in which respective lower electrodes and respective upper electrodes for the plural cells are electrically connected for each of the upper and lower sides; namely in which the plural cells share one lower electrode, and the respective upper electrodes for the plural cells are electrically connected to each other). As discussed above, the structure of the force sensor can be expressed below from another point of view. A support for one element is made up of plural parts and, corresponding to the plural parts of the support, a movable member (membrane), the upper electrode, and the gap are each separated into plural parts. Furthermore, in the one element including one group of the respective plural parts, the plural parts of the upper electrode are electrically connected to each other. The reason why deformation of the membrane with respect to the load can be reduced by employing the above-mentioned structure will be described below.

FIGS. 2A, 2B and 2C are illustrations to explain a relation of an amount of deformation of the membrane with respect to a shape of the membrane and a load in the force sensor of the present invention. Components similar to those in FIGS. 1A to 1C are denoted by the same reference symbols. FIG. 2A is a sectional view of a membrane 201. The membrane 201 represents a composite unit of the membrane 105a and the upper electrode 107, which are illustrated in FIGS. 1A to 1C. It is assumed that the composite unit has a Young's modulus E and a Poisson's ratio nu. It is also assumed, as illustrated in FIG. 2B, that the cells, i.e., the membranes 201, each have a circular shape and are arranged in a square lattice pattern in the form divided into N pieces for each side of a square element with one side having a length of 2 A.

FIG. 2C is a sectional view of one of the N-divided membranes. Assume that a sensor area, i.e., an area of a region where the sensor has sensitivity for a load, is denoted by S, and the radius of the membrane 201 is denoted by a. When a load F is evenly applied to the element, a pressure P exerted on the membrane 201 is expressed by the following formula.

$$S=4A^2 \tag{1}$$

$$a=A/N \tag{2}$$

$$P=F/S=F/(2A)^2 \tag{3}$$

Assuming a membrane thickness to be t, a deformation amount delta caused by the exertion of the pressure P at a point spaced through a distance r from a cell center of the membrane 201 in the radial direction is expressed by the following formula.
[Math. 1]

$$\delta = 3/16 \cdot ((1-\nu^2)/(E \cdot t^3)) \cdot ((A/N)^2 - r^2)^2 \cdot P \tag{4}$$

In the formula (4), the deformation amount delta is maximized at r=0, i.e., at the center of the membrane 201. Assuming the maximum deformation amount to be delta-max, the following formula is obtained.
[Math. 2]

$$\delta\max = 3/16 \cdot ((1-\nu^2)/(E \cdot t^3)) \cdot (A/N)^4 \cdot P \tag{5}$$

From the formula (5), it is understood that, by dividing the element into N pieces, the deformation amount delta-max of the membrane reduces in reverse proportion to the fourth power of the number N of divisions as expressed by the following formula.
[Math. 3]

$$\delta\max \propto 1/N^4 \tag{6}$$

For the reason discussed above, a force sensor can be realized in which the deformation amount delta with respect to the load F is small.

The substrate 102 may be a glass substrate instead of being made of single-crystal silicon. When the substrate 102 is made of an insulating material, the insulating layer 103 may be omitted. The insulating layer 103 may be formed, instead of thermally oxidizing single-crystal silicon, by depositing a silicon oxide film or a silicon nitride film with the plasma CVD method, or by depositing a silicon nitride film with the low-pressure CVD method. The lower electrode 104, the upper electrode 107, and the upper electrode wiring layer 108 may be formed by, instead of vacuum deposition of Al, vacuum deposition of Ti, Cr, Au, Cu or Ni, or sputtering of Al, Ti, Cr, Au, Cu or Ni. The above-mentioned materials may be formed in a multilayer structure. When the materials are formed in a multilayer structure, an improvement in adhesion and controllability of film stress can be expected. When the substrate 102 has electrical conductivity and the electrical conductivity is utilized for the lower electrode, the substrate 102 may be used as the lower electrode while the lower electrode 104 is omitted. The gap 106 may have, instead of the circular shape illustrated in FIG. 1A, a triangular, rectangular, or polygonal shape. Moreover, the gaps 106 for all the cells are not required to be spatially independent of one another, part or the whole of the gaps 106 may be spatially connected through paths.

The surface material made of the elastic body will be described below. The surface material made of the elastic body can be formed by a method of coating a thermosetting material over the surface of the force sensor 101, and then applying heat to harden the coated thermosetting material. Such a method can be applied to the case of primarily employing silicone rubber. In an alternative method, an elastic body material is previously prepared in the form of a sheet, and is then fixed to a chip of the force sensor 101 by employing an adhesive. The adhesive may be in the form of, for example, a thermosetting adhesive, a room-temperature setting adhesive, or a tape coated with an adhesive. With this method, a process of composing and molding materials of the elastic body and a process of manufacturing the sensor chip can be performed separately from each other, and therefore restrictions on temperature, pressure, etc. during those processes are avoided from causing influences mutually. In still another method, a sensor chip including an elastic body material and a primer adhesive, which are put on the sensor chip, is placed into a clave and is hardened by baking. This method is featured in providing a stronger bonding force between the elastic body and the sensor chip than that obtained with the other forming methods.

The thickness of the elastic body is preferably larger than the height of the gap 106. If the thickness of the elastic body is smaller than the height of the gap 106, there is a possibility that, before the membrane 105*a* and the lower electrode 104 are contacted with each other due to the load applied from the workpiece, the workpiece comes into contact with the sidewall 105*b* of the membrane, thereby impeding the deformation of the membrane. The height of the gap 106 is generally in the range of 50 nanometers to 10 micrometers. On the other hand, as the thickness of the elastic body increases, the load applied from the workpiece tends to distribute to a larger extent, or the elastic body tends to more easily deform due to a force acting in a direction along the sensor surface (i.e., a force in the shearing direction). From the above-mentioned point of view, it is preferable that the elastic body is relatively thin. The thickness of the elastic body is further restricted by the method of forming the elastic body. When the above-described methods are used, the elastic body can be easily formed on condition that it has a thickness of 100 micrometers or more. From the reason discussed above, the thickness of the elastic body is practically 100 micrometers or more.

While, in the first embodiment, the elastic body 123 is formed to continuously cover all the cells, the elastic body 123 may cover the cells in a state divided per element. Furthermore, the elastic body 123 may be formed to extend in a direction toward the flexible substrate 114, illustrated in FIGS. 1A and 1B, such that the elastic body 123 serves also as the wire protection member 122. The silicon nitride film or the silicon oxide film has hardness ranging from several tens to 200 GPa in terms of the Young's modulus, whereas the elastic body 123 is preferably softer than such a level of hardness. An actually formed film of silicone rubber, EPDM (ethylene-propylene rubber), PDMS (poly(dimethylsiloxane)), or urethane rubber has hardness ranging from 1 MPa to 1 GPa in terms of the Young's modulus. When the grasped workpiece is deformed following the membrane layer 105 and the upper electrode 107 due to the grasping force, the elastic body 123 may be omitted. When it is desired for the surface of the surface material made of the elastic body to have appropriate roughness from the viewpoint of grasping the workpiece, the relevant surface may be given with a certain level of roughness.

With reference to FIGS. 2A to 2C, an example has been described in which plural cells having the same shape are arranged at equal intervals in the element having a square shape. However, the advantageous effect of reducing the deformation amount of the membrane positioned over the gap can be obtained even when cells having different shapes are arranged, or even when the plural elements are each in a polygonal or circular shape, or when they are in combination of polygonal and circular shapes.

Second Embodiment

FIGS. 3A, 3B and 3C are illustrations to explain a structure of a second embodiment of the force sensor according to the present invention. FIG. 3A is a plan view, FIG. 3B is a sectional view taken along IIIB-IIIB, and FIG. 3C is a sectional view taken along IIIC-IIIC.

A force sensor 301 includes a substrate 302, an insulating layer 303, a post (support) 304, a membrane layer 305, a gap 306, an upper electrode 307, a lead wiring 308, and pads 309 and 310. The force sensor 301 further includes a flexible substrate 311, pads 312 and 313, wires 314 and 315, a device board 316, a wire protection member 317, and an elastic body 318.

The substrate 302 is an electrically-conductive plate-like material made of single-crystal silicon, and it functions as a lower electrode. The insulating layer 303 is formed on the substrate 302. The insulating layer 303 can be formed by thermally oxidizing the substrate 302 made of single-crystal silicon. The post 304 is formed in a part of the insulating layer 303. The post 304 functions not only as a support for supporting the membrane layer 105, which is positioned over the gap 306, in a movable state, but also as a spacer for keeping the membrane layer 305 away from a bottom surface in the gap 306.

The membrane layer 305 is a film of single-crystal silicon, and a part of the membrane layer 305 is connected to the insulating layer 303 through the post 304. As illustrated in FIG. 3B, the gap 306 is defined between the insulating layer 303 and the membrane layer 305 in a region where the post 304 is not present. Such a structure of the membrane layer 305 can be formed by the following method. First, the substrate 302 is thermally oxidized to form a silicon oxide film, and the silicon oxide film is partly removed into the shape of the gap 306 by etching. The post structure is thus formed. The membrane layer 305 is then obtained by directly bonding the surface of a handle layer of an SOI substrate to the surface of the post structure, and removing both the handle layer and a box layer of the SOI substrate by etching. Regions of the membrane layer 305, the regions being positioned above the individual gaps 306, are denoted by 305*a*, 305*b*, etc.

The upper electrode 307 is an electrode formed on the membrane layer 305, and it can be formed by vacuum deposition of Al. In the example of FIG. 3A, the gap 106 has a circular shape and has a typical diameter of from 10 micrometers to several hundred micrometers. A typical thickness of the membrane 305*a* is from 100 nanometers to several micrometers, and a typical thickness of the upper electrode 307 is from 10 nanometers to several micrometers. Accordingly, the membrane 305*a* has flexibility together with the upper electrode 307. Note that the above-mentioned ranges of the diameter and the thickness are to be taken as illustrative and not as restrictive. The membrane 305*a* and the upper electrode 307, which are disposed above one gap 306, constitute a cell that is a minimum constituent unit of a detection device for detecting a load. One force sensor 301 includes a plurality of cells, and an element includes one or more cells. The force sensor 301 is required to include one or more elements, but it preferably includes a plurality of elements. In the latter case, the force sensor can measure a load distribution. FIG. 3A illustrates the example in which two elements, each including nine cells, are arranged in the direction of each side of the force sensor.

In the example of FIGS. 3A to 3C, since the lower electrode is constituted by the substrate 302, all the cells are electrically connected to each other at the lower electrode. Furthermore, in parts of the plural cells per group, respective upper electrodes are electrically connected to each other. An assembly of the cells per group constitutes one element. In FIGS. 3A to 3C, an assembly of the cells, each including the upper electrode formed as an upper electrode 307a, constitutes one element, and an assembly of the cells, each including the upper electrode formed as an upper electrode 307b, constitutes one element. Thus, the force sensor of this embodiment is featured in that plural cells are electrically connected to constitute one element. Stated in another way, the element is constituted by connecting a plurality of variable capacitors in parallel, and is a minimum unit for detection of the load.

For each element, the upper electrodes 107 are led out to the pad 309 through the lead wiring 308. The pad 310 is formed on the substrate 302. The insulating layer 303 is opened at a position above the pad 310 such that the surface of the pad 310 is exposed to the outside. The substrate 302 is fixed onto the device board 316. The flexible substrate 311 is also fixed onto the device board 316. On the flexible substrate 311, the pads 312 and 313 are disposed in opposing relation to the pads 309 and 310, respectively, and the former pads are connected to the latter pads through the wires 314 and 315, respectively. The wire protection member 317 is disposed around those bonded wires to reduce damage that may be caused by external environments.

A surface material made of the elastic body 318 is coated over an upper surface in a region where the cells are arranged. The elastic body 318 can be made of a similar material to that of the elastic body 123 in the first embodiment, and therefore description of the material of the elastic body 318 is omitted here. The elastic body 318 has the function of distributing, to the membrane layer 305, a load that is applied upon the workpiece contacting with the sensor surface. With the function of the elastic body 318, even when the surface of the workpiece contacts with the post 304 and impedes deformation of the membrane 305a, the load can be detected because the elastic body 318 is deformed along the membrane 305a and the membrane 305a is hence deformed. The reason why the deformation of the membrane with respect to the load can be reduced is similar to that described above in the first embodiment, and therefore description of the reason is omitted here.

Third Embodiment

FIG. 4 illustrates a third embodiment in which a grasping device is constituted by employing the force sensor of the present invention. A hand 401 has a plurality of fingers 402. The fingers 402 include mechanisms capable of causing the fingers 402 to translate or rotate to change the spacing between the fingers 402 in such a way of grasping a workpiece 405. A force sensor 403 is disposed on at least one of the plural fingers 402 at a position where the workpiece 405 contacts with the finger 402. The force sensor described above in the first embodiment or the second embodiment can be employed as the force sensor 403. A pad 404 is disposed on one or more of the fingers 402 not including the force sensors 403. Similarly to the force sensor 403, the pad 404 is disposed at a position where the workpiece 405 contacts with the finger 402.

The pad 404 serves to make the surface shape, the friction coefficient, and the elasticity modulus of the finger 402, which does not include the force sensor 403, similar to those of the finger 402 including the force sensor 403. To that end, for example, the former finger is preferably coated with the elastic body 123 in the first embodiment or the elastic body 318 in the second embodiment. While FIG. 4 illustrates the example in which the force sensor 403 is disposed on only one of the plural fingers, the force sensors may be disposed on plural fingers. In such a case, a workpiece grasping posture, such as eccentricity of a position where the workpiece is grasped, can be detected by comparing outputs of the plural sensors.

The example of FIG. 4 illustrates the case where the grasping operation of the fingers 402 is performed by narrowing the distance between the fingers 402 to grasp the workpiece 405. However, the force sensor 403 can be further applied to an operation of inserting a plurality of fingers into the inside of a ring-shaped workpiece, and then widening the distance between the fingers to grasp the workpiece, or to an operation of moving a workpiece to slide in astute where the finger is contacted with the workpiece. Stated in another way, the force sensor can be utilized in a device for handing an object in a broad sense, and can be used to control the handling of the object in accordance with a which represents a contact load with respect to the object and which is output from the force sensor. In any of the above-mentioned applications, the force sensor 403 is just required to be arranged between the finger and the workpiece. The workpiece is a material object, such as a solid body having certain rigidity, and it may take various kinds of forms, such as a metal piece, a balloon-like object, a jelly-like material, and a living thing.

An output of the force sensor 403 is converted to an electrical signal through a sensor circuit 406. The sensor circuit 406 is a circuit that detects the capacitance between the upper and lower electrodes of the force sensor. In a preferable example, the sensor circuit 406 includes, e.g., an oscillation circuit that applies an AC voltage signal to the force sensor 403, a detection circuit that converts a current flowing through the force sensor to a voltage signal, and a detector circuit that detects an envelope curve of an output (AC voltage signal) of the detection circuit. From the viewpoint of principle for operation, however, the sensor circuit 406 is just required to include an oscillation circuit that applies an AC voltage, and a circuit that detects the magnitude of a current flowing between the upper and lower electrodes of the force sensor. The AC voltage signal preferably has a frequency sufficiently away from the natural frequency of the movable member including the upper electrode, the movable member being positioned above the gap. With that setting, the movable member is substantially not vibrated, and the workpiece contact load can be accurately detected regardless of the state of the workpiece (i.e., regardless of whether the workpiece is a stationary state or a dynamic state relative to the force sensor).

The output of the sensor circuit 406 is input to a comparator 407. A target value of the grasping force (i.e., a grasping force torque signal) is also input to the comparator 407, and a value obtained by subtracting the output value of the sensor circuit 406 from the target value of the grasping force, i.e., a deviation amount, is output to a controller 408. The controller 408 generates, depending on the deviation amount input thereto, a signal for driving the fingers 402 of the hand 401.

According to the present invention, since the membrane or the movable member in each of detection unit devices is divided into plural parts, an area of the membrane in each of the divided parts can be designed freely. Hence the deformation amount of the membrane for a unit load can be reduced by reducing the area of the membrane in each of the divided parts. As a result, the force sensor can be realized in which the deformation amount of the deformable portion in the sensor surface is smaller than that in the related art.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

INDUSTRIAL APPLICABILITY

The present invention can be applied to, e.g., a force sensor that detects the magnitude and the distribution of a contact load, for example.

REFERENCE SIGNS LIST 101, 301 force sensors
102, 302 substrates
104 lower electrode
105, 305 membrane layers
105b, 304 support (sidewall, post, or spacer)
106, 106a, 106b, 306 gaps
107, 107a, 107b, 307 upper electrodes
123, 318 elastic bodies

The invention claimed is:

1. A capacitive force sensor for measuring based on contacting with an object, comprising:
a plurality of cells each including a lower electrode, a movable member that includes an upper electrode and has flexibility, and a support arranged to movably support the movable member and to form a gap between the upper electrode and the lower electrode,
wherein the plural cells are grouped into elements each including at least the plural cells, and in a same element, the lower electrodes are electrically connected to each other and the upper electrodes are electrically connected to each other, and between different elements, at least ones of the upper electrodes and the lower electrodes are electrically separated from each other; and
wherein at least a part of the elements is covered at its surface with an elastic body having a smaller longitudinal elasticity modulus than that of the support, and
wherein the thickness of the elastic body is larger than a height of the gap.

2. The force sensor according to claim 1, wherein the elastic body is selected from among silicone rubber, EPDM (ethylene-propylene rubber), PDMS (poly(dimethylsiloxane)), and urethane rubber.

3. The force sensor according to claim 1, wherein the lower electrode is disposed on a substrate.

4. The force sensor according to claim 1, wherein the upper electrode is supported by a membrane having flexibility, and the support supports the membrane.

5. The force sensor according to claim 1, wherein the support is made of silicon oxide or silicon nitride.

6. The force sensor according to claim 1, further comprising an oscillation circuit that applies an AC voltage between the upper electrode and the lower electrode, and a circuit that detects a magnitude of a current flowing between the upper electrode and the lower electrode.

7. The force sensor according to claim 6, wherein the circuit detecting the magnitude of the current includes a circuit that converts the current flowing between the upper electrode and the lower electrode to a voltage signal, and a circuit that detects an envelope curve of the voltage signal.

8. A device configured to handle an object,
wherein the force sensor according to claim 1 is disposed in a portion of the device, the portion being contacted with the object and used to handle the object, and
the handling of the object is controlled by employing a signal that is output from the force sensor, and that is related to a contact load with respect to the object.

9. A grasping device configured to grasp an object,
wherein the force sensor according to claim 1 is disposed in a portion of the grasping device, the portion being contacted with the object and used to grasp the object, and
a handling force to grasp the object is controlled by employing a signal that is output from the force sensor, and that is related to a contact load with respect to the object.

10. The capacitive force sensor according to claim 1, wherein the thickness of the elastic body is 100 micrometers or more.

11. The capacitive force sensor according to claim 1, wherein the elastic body covers all the elements.

12. The capacitive force sensor according to claim 11, wherein the elastic body continuously covers all the elements.

13. The capacitive force sensor according to claim 11, wherein the elastic body covers all the elements in a state divided per element.

* * * * *